(12) United States Patent
Borillo

(10) Patent No.: US 12,357,737 B2
(45) Date of Patent: Jul. 15, 2025

(54) DEGASSING UNIT

(71) Applicant: DIALITY INC., Irvine, CA (US)

(72) Inventor: Brandon Borillo, Irvine, CA (US)

(73) Assignee: DIALITY INC., Irvine, CA (US)

( * ) Notice: Subject to any disclaimer, the term of this patent is extended or adjusted under 35 U.S.C. 154(b) by 9 days.

(21) Appl. No.: 18/414,850

(22) Filed: Jan. 17, 2024

(65) Prior Publication Data

US 2024/0307597 A1 Sep. 19, 2024

Related U.S. Application Data

(63) Continuation of application No. 17/824,356, filed on May 25, 2022, now Pat. No. 11,904,079.

(60) Provisional application No. 63/194,834, filed on May 28, 2021.

(51) Int. Cl.
| | |
|---|---|
| *A61M 1/16* | (2006.01) |
| *A61M 1/14* | (2006.01) |
| *B01D 15/38* | (2006.01) |
| *B01D 19/00* | (2006.01) |

(52) U.S. Cl.
CPC .......... *A61M 1/1658* (2013.01); *A61M 1/156* (2022.05); *A61M 1/1694* (2013.01); *B01D 15/38* (2013.01); *B01D 19/0031* (2013.01); *B01D 19/0057* (2013.01)

(58) Field of Classification Search
None
See application file for complete search history.

(56) References Cited

U.S. PATENT DOCUMENTS

| | | |
|---|---|---|
| 5,194,158 A | 3/1993 | Matson |
| 2011/0092875 A1 | 4/2011 | Beck |
| 2014/0090557 A1 | 4/2014 | Gottlied et al. |
| 2014/0157983 A1 | 6/2014 | Trump et al. |
| 2014/0216250 A1 | 8/2014 | Meyer et al. |
| 2014/0217028 A1 | 8/2014 | Pudil et al. |
| 2016/0166751 A1 | 6/2016 | Meyer et al. |
| 2021/0128807 A1 | 5/2021 | Poppe et al. |

FOREIGN PATENT DOCUMENTS

| | | |
|---|---|---|
| DE | 102004040950 A1 | 3/1996 |
| WO | WO 8500532 A | 2/1985 |

OTHER PUBLICATIONS

WO, PCT/US22/30876 ISR and Written Opinion, Dec. 1, 2022.

*Primary Examiner* — Krishnan S Menon
(74) *Attorney, Agent, or Firm* — ONE LLP

(57) ABSTRACT

A degassing module that may be used in conjunction with a sorbent regeneration cartridge is described. The degassing module may include an air inlet port, a fluid outlet port, a gas outlet port, first and second channels located in an interior chamber, a port connecting the first and second channels, and a hydrophobic membrane positioned above the second channel. The first channel may be in fluid communication with the air inlet port and the second channel may be in communication with the fluid outlet port. In some embodiments, each of the first and second channels may have a spiral configuration.

16 Claims, 6 Drawing Sheets

DEGASSING UNIT

CROSS-REFERENCE TO RELATED APPLICATION

This application is a continuation of U.S. application Ser. No. 17/824,356, filed May 25, 2022, which claims priority to, and the benefit of, U.S. Provisional Application No. 63/194,834, filed May 28, 2021, both of which are hereby expressly incorporated by reference in their entireties for all purposes.

BACKGROUND OF THE INVENTION

The present invention relates to cartridges that are useful in dialysis. In particular, the present invention relates in general to the degassing of regenerated dialysate fluids.

More than 1 in 7 adults in the U.S. (approximately 15% of U.S. adults) are estimated to have chronic kidney (or renal) disease. In people who suffer from chronic kidney disease, their kidneys no longer clean their blood as well as healthy kidneys. Thus, toxic waste and extra fluid accumulates in the body. Dialysis is a treatment that removes the waste products and excess fluid that accumulate in the blood as a result of kidney failure. Chronic renal failure is when the renal function has deteriorated to about 25% of normal. This amount of deterioration causes significant changes in the blood chemistry and is about the time that people feel poorly enough that they seek medical care. If medical treatment is sought at that time, progression can be slowed. Late-stage chronic renal failure is when kidney function has decreased to 15%. End stage renal failure is when kidney function is at 5% of normal. Death will most likely result without treatment at this point.

Although there is no current cure for renal disease, there are several forms of treatment. One treatment is transplantation, which is where a human kidney is surgically placed in the body and connected to the bladder. After transplantation, daily medication is needed to keep the body from rejecting the transplanted kidney. Another treatment is peritoneal dialysis (PD). With this treatment, a mild saltwater solution containing dextrose and electrolytes called dialysate is put into the peritoneal cavity. Because there is a rich blood supply to this abdominal cavity, urea and other toxins from the blood and fluid are moved into the dialysate, thereby cleaning the blood. The dialysate is then drained from the peritoneum. Later "fresh" dialysate is again put into the peritoneum.

Another form of treatment is hemodialysis. This is a method of blood purification in which blood is continually removed from the body and passed through a dialyzer (artificial kidney) where metabolic waste and excess water are removed and pH and acid/base balance are normalized. The blood is simultaneously returned to the body. The dialyzer is a small disposable device consisting of a semipermeable membrane. The membrane allows the wastes, electrolytes, and water to cross but restricts the passage of large molecular weight proteins and blood cells. Blood is pumped across one side of the membrane as dialysate is pumped in the opposite direction across the other side of the membrane. The dialysate is highly purified water with salts and electrolytes added. The machine is a control unit that acts to pump and control pressures, temperatures, and electrolyte concentrations of the blood and the dialysate. The average length of one hemodialysis treatment is about 3.5 hours.

There are several types of hemodialysis-including single pass systems and sorbent systems. Single pass hemodialysis is the most common treatment for renal disease. These instruments are called single pass because the dialysate (cleaning solution) passes by the blood in the dialyzer one time and then is disposed. Single pass dialysis machines generally require: (1) a water source capable of delivering at least 1000-1500 ml/min (assuming a 50% rejection rate by the reverse osmosis (R.O.) system); (2) a water purification system sufficient of providing a continuous flow of 500-800 ml/min of purified water, (3) an electrical circuit of at least 15 amps in order to pump and heal 500-800 ml of water/min, and (4) a floor drain or any other receptacle capable of accommodating at least 500 ml of used dialysate/minute as well as the rejected water from the R.O. system.

Sorbent dialysis systems do not require a continuous water source, a separate water purification machine, or a floor drain because the system continuously regenerates a small volume of dialysate and incorporates a water treatment system within the machine. Therefore, sorbent systems are portable. The sorbent system can use 6 liters of water from which dialysate is made for an entire treatment. The sorbent system uses a sorbent cartridge, which acts both as a water purifier and as a means to regenerate used dialysate into fresh dialysate. The infusate system acts with the sorbent system to properly balance the electrolyte composition of the regenerated dialysate.

Currently, there are several types of multi-layer sorbent cartridges used in dialysis machines that remove uremic toxins from patient's blood and reuse the dialysate solution via recirculation. These sorbent dialysis systems, however, do not efficiently remove uremic toxins at a high capacity or with a high electrolyte stability.

In a sorbent dialysis system, the process of removing urea with urease and zirconium phosphate generates a fluid composition leaving the sorbent cartridge that has a lower pH than the standard range used in bicarbonate dialysis. Previous sorbent devices have used high pH final layers in sorbent cartridges of zirconium oxide and zirconium carbonate. These devices, however, have limitations on dialysate flow rate and dialysis treatment length that must be traded off against increasing the total mass of the final layers in order to raise the pH. Alternatively, an increased pH can be used in the zirconium phosphate layer(s). Other metals phosphates of iron (III), titanium (IV) and cerium (IV) suffer from similar issues. This, however, results in excessive sodium and reduced removal capacity for the ammonium generated by the urea reaction with urease. Other processes have used sodium bicarbonate as an added chemical to the sorbent outlet stream, but these systems either have resultant pH levels well below standard bicarbonate dialysis or require specialized systems for the removal of a majority of the dissolved $CO_2$ gas in the fluid stream leaving the sorbent cartridge.

Some devices removed $CO_2$ by pumping dialysate into an open chamber and allowing bubbles to float to the top of the chamber. This system, however, only relies on gas naturally exiting the fluid while agitating the fluid with a pump. Such a system affords less control over the degassing process. Moreover, the fluid reservoir is open to the atmosphere, which presents potential sterility issues, extra short-term maintenance, and long-term maintenance issues.

Other degassing systems that remove $CO_2$ under vacuum are not ideal because they require a lot of energy to operate. Moreover, a lot of water evaporates under these vacuum systems, which concentrates the dialysate causing sodium levels to rise. They also create a stream of moisture that needs to be collected and disposed. A vacuum system also adds larger vacuum pressure requirements on system tubing and pumps. Membrane degassing systems require large surface area and expensive membranes that are prone to fouling issues. Degassing with a chemical reaction or with an adsorbent adds considerable cost and most feasible sorbents for $CO_2$ also leach undesired chemicals.

Accordingly, in the area of dialysis, it would be beneficial to create a sorbent regeneration system that includes an effective method of removing excess $CO_2$ gas from the regenerated fluid while also raising the pH of the fluid to an acceptable level.

SUMMARY

Figure 1A:
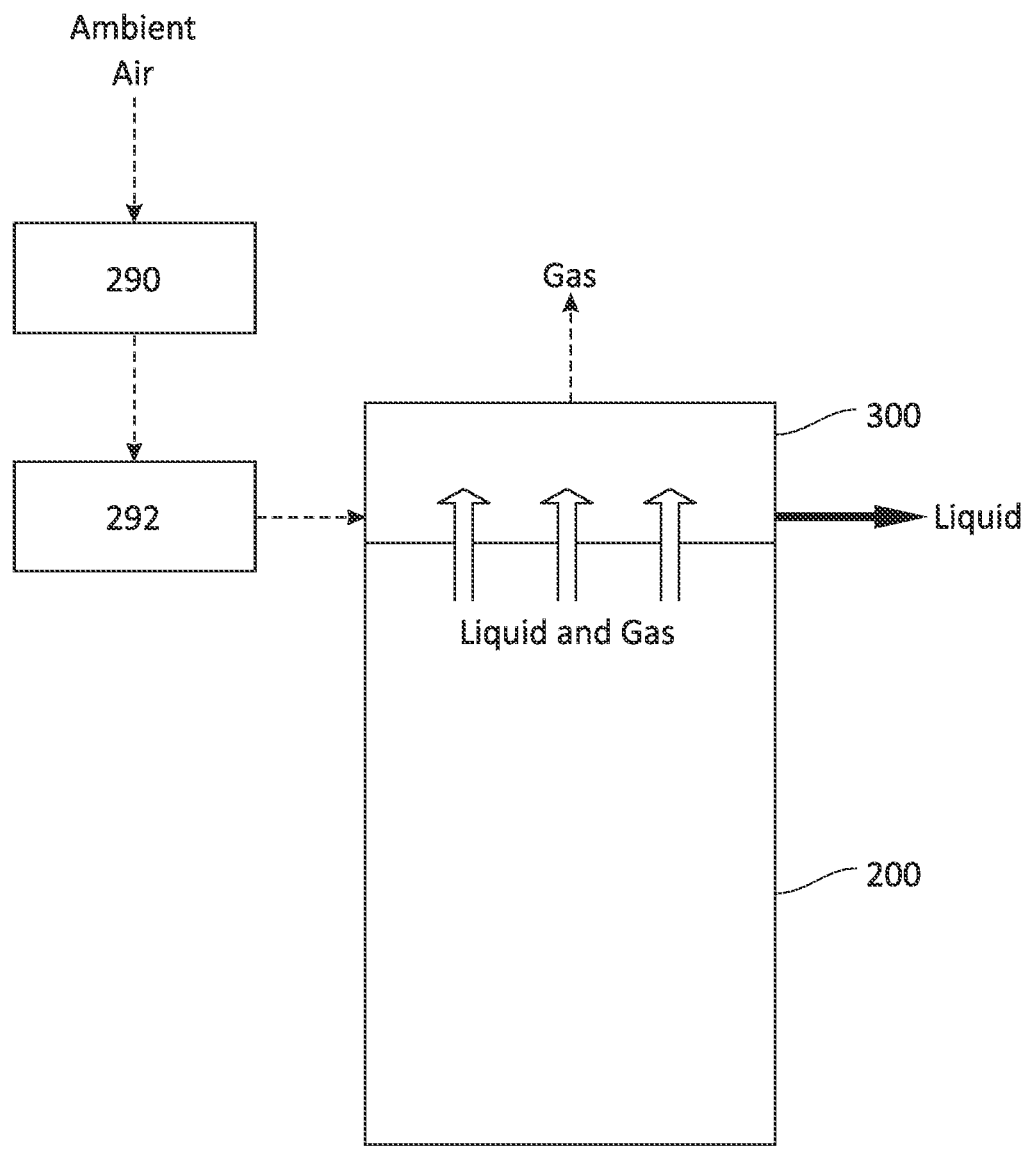
FIG. 1A is an exemplary diagram of a sorbent cartridge with a degasser module.

A sorbent cartridge, which includes a degassing module, is described that can be used to regenerate dialysate to be used in a dialysis system.

Sorbent regeneration degassing may be accomplished by introducing a stream of air, which may be substantially free of $CO_2$, into the regenerated dialysate. The stream of air may have about the same approximate flowrate as the flowrate of the liquid. The combined air-liquid fluid may then be exposed to a hydrophobic membrane where the gas is free to exit the system.

The fluid may be directed to flow through several fluid channels. In a first fluid channel, the fluid may be mixed with ambient air to lower the partial pressure of $CO_2$ in the fluid. In a second fluid channel, as the fluid flows through the long channel, at least a portion of the gas contained in the fluid dissipates out of the fluid through a hydrophobic membrane.

DETAILED DESCRIPTION

In a dialysis treatment, a dialysis machine functions as an artificial kidney to remove uremic toxins, balance ionic molecules, and equilibrate pH for patients that lack healthy kidneys to perform those tasks. With the substitution of a multi-layer cartridge for a large volume of water, the cartridge is responsible for not only removing uremic toxins, but also balancing ionic salts and pH.

A hemodialysis system that incorporates a dialysate generator is described in US 2021/0128807, which is hereby expressly incorporated by reference in its entirety for all purposes. Various embodiments of a sorbent regeneration system, which includes a sorbent cartridge, described herein may be incorporated into the system described in US 2021/0128807 in place of the dialysate generator.

A sorbent regeneration cartridge 200 may include multiple layers of components to clean the dialysate. The cartridge 200 may at least include a layer of urease and a layer or layers of zirconium phosphate, or other metal phosphates such as iron (III), titanium (IV), and cerium(IV), which may be in different forms. During regenerative dialysis, the used dialysate moves up through the layers of the cartridge 200. The urease converts urea into ammonium carbonate. The ammonia and ammonium ions are then removed by the zirconium phosphate (or metal phosphate) layer or layers in exchange for $H^+$ and $Na^+$ ions. The carbonate from the urea hydrolysis then combines with $H^+$ to form bicarbonate ($HCO_3^-$) and carbonic acid ($H_2CO_3$). Carbonic acid is an unstable organic acid; most of it quickly breaks down into water and carbon dioxide molecules ($CO_2$). The $CO_2$ gas bubbles may then be vented from the cartridge using degassing unit 300.

The sorbent cartridge 200 has two processes that create an excess amount of carbon dioxide ($CO_2$) gas. The breakdown of urea ($CON_2H_4$) by the urease enzyme follows the reactions below:

$$CON_2H_4 + H_2O \rightarrow CO_2 + 2NH_3$$

$$CO_2 + 2NH_3 H_2O \rightarrow 0.5CO_3^{2-} - HCO_3^{1-} + 2NH_4^{1+}$$

The chemical equilibrium may have different amounts of each form of carbon, ammonia ($NH_3$), and ammonium ($NH_4^+$) depending on the solution pH:

$$xCO_2 \leftarrow \rightarrow yHCO_3^{1-} \leftarrow \rightarrow zCO_3^{2-}$$

$$aNH_3 \leftarrow \rightarrow bNH_4^{1+}$$

When the spent dialysate, which contains ammonia ($NH_3$), then passes through the zirconium phosphate (or other metal phosphate) cation adsorbent, the following reaction occurs, which results in the production of carbonic acid ($H_2CO_3$).

$$Zr(HPO_4)_2 + 0.5CO_3^{2-} - HCO_3^{1-} + 2NH_4^{1+} \leftarrow \rightarrow Zr(NH_4PO_4)_2 + HCO_3^{1-} + H_2CO_3$$

To a lesser extent sodium bicarbonate and sodium chloride can also exchange to produce carbonic acid.

$$Zr(HPO_4)_2 + NaHCO_3 + NaCl \leftarrow \rightarrow Zr(NaPO_4)(HPO_4) + H_2CO_3 + NaCl$$

Carbonic acid ($H_2CO_3$) is not stable and tends to breakdown into carbon dioxide ($CO_2$), according to the following equation:

$$H_2CO_3 \rightarrow CO_2 + H_2O$$

Thus, treatment of the dialysate with the zirconium phosphate or other metal phosphates such as iron (III), titanium (IV) and cerium (IV) results in an acidified dialysate solution. A portion of the $CO_2$ present may be in a purely gaseous phase and another portion of the $CO_2$ present may be dissolved in the dialysate exiting the sorbent cartridge 200. The portion of $CO_2$ dissolved in the dialysate may be very high because the partial pressure of $CO_2$ in the sorbent cartridge is very high. This relationship is known as Henry's law:

$$H^{cp} = \frac{C_i}{P_i}$$

In Henry's Law, a constant ($H^{cp}$) relates the concentration of a dissolved gas ($C_i$) to the partial pressure of that same dissolved gas ($P_i$). Thus, methods to remove excess $CO_2$ may focus on lowering the partial pressure of $CO_2$ in the dialysate.

Figure 1B:
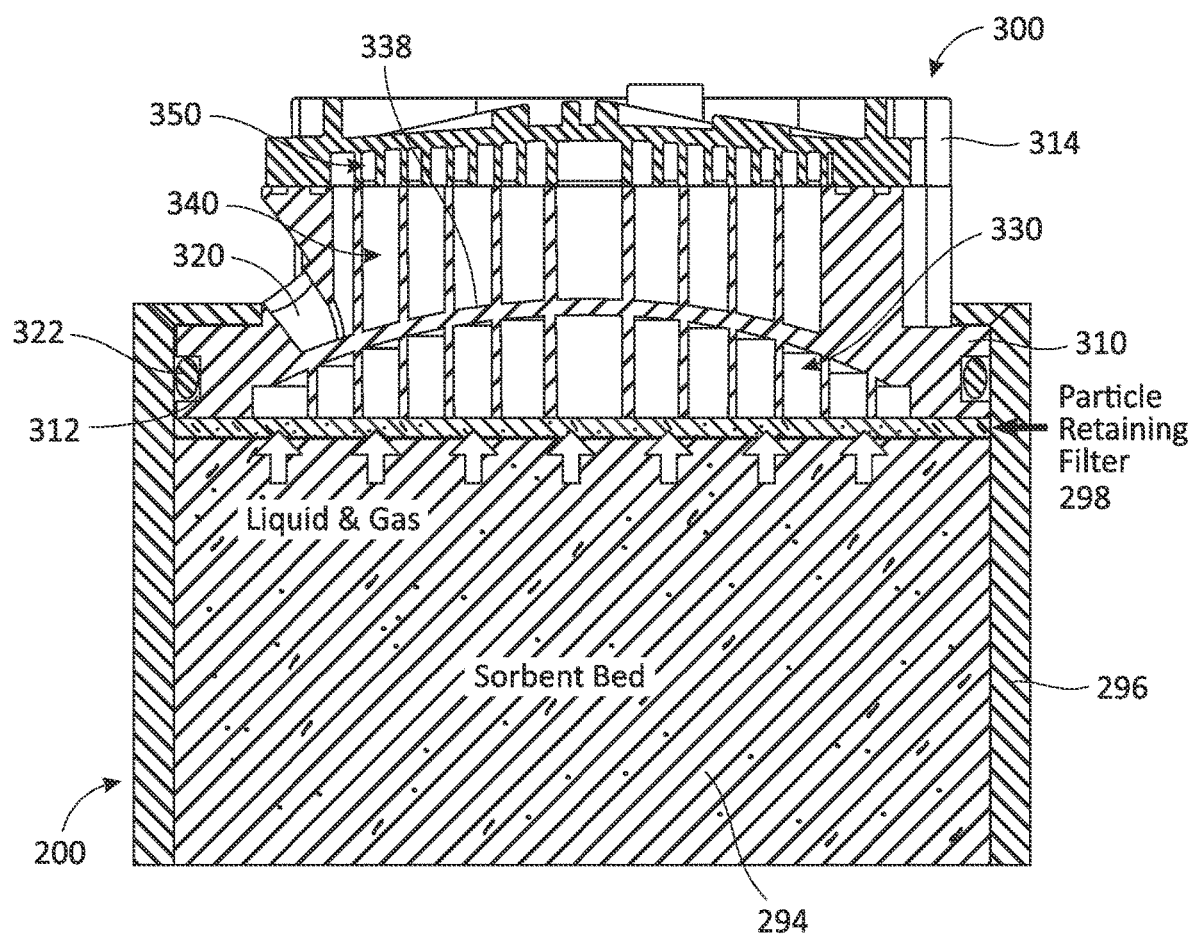
FIG. 1B is a cross-section of an exemplary sorbent cartridge with a degasser module.
Figure 3A:
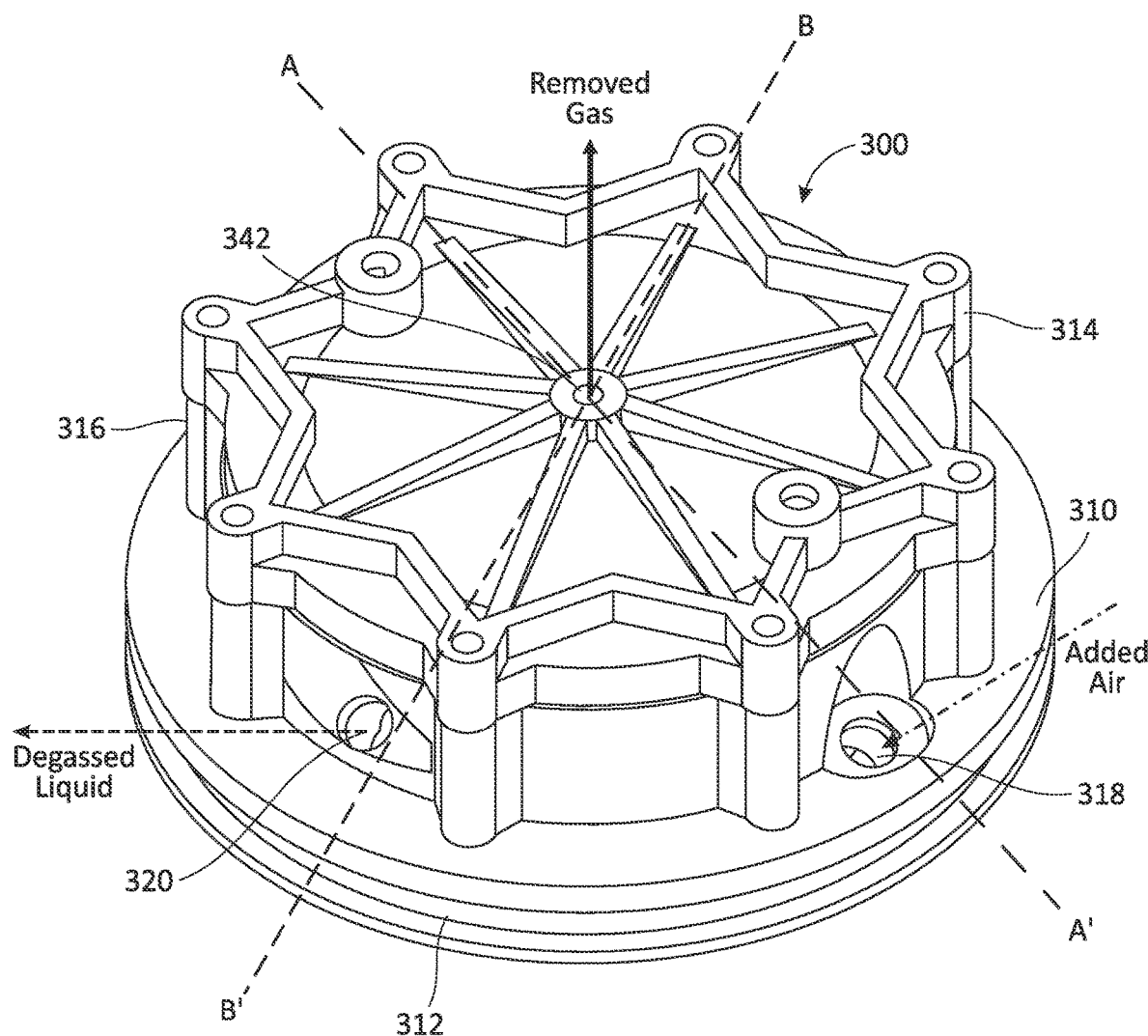
FIG. 3A is a perspective view of a degasser module.

As seen in FIGS. 1A-1B and FIG. 3A, a degasser module or unit 300 may be located on top of a sorbent cartridge 200. The degasser 300 may include a container 316 having a base 310 and a cover 314. The base may have a groove 312 configured to hold an O-ring 322, which can frictionally engage an outer wall 296 of the sorbent cartridge 200. Container 316 may contain at least two fluid channels, a lower fluid channel 330 and an upper fluid channel 340, which are configured to direct flow of a fluid, such as regenerated dialysate. The base 310 of the degasser unit 300 may sit adjacent to or in contact with the particle retaining filter 298 that sits atop the sorbent bed 294 such that the lower fluid channel may be in contact the particle retaining filter 298 at the top of the sorbent bed 294. Thus, the lower fluid channel 330 may be in contact with the fluid and gas that is being pumped from the bottom to the top of the sorbent bed 294 of sorbent cartridge 200.

Figure 2A:
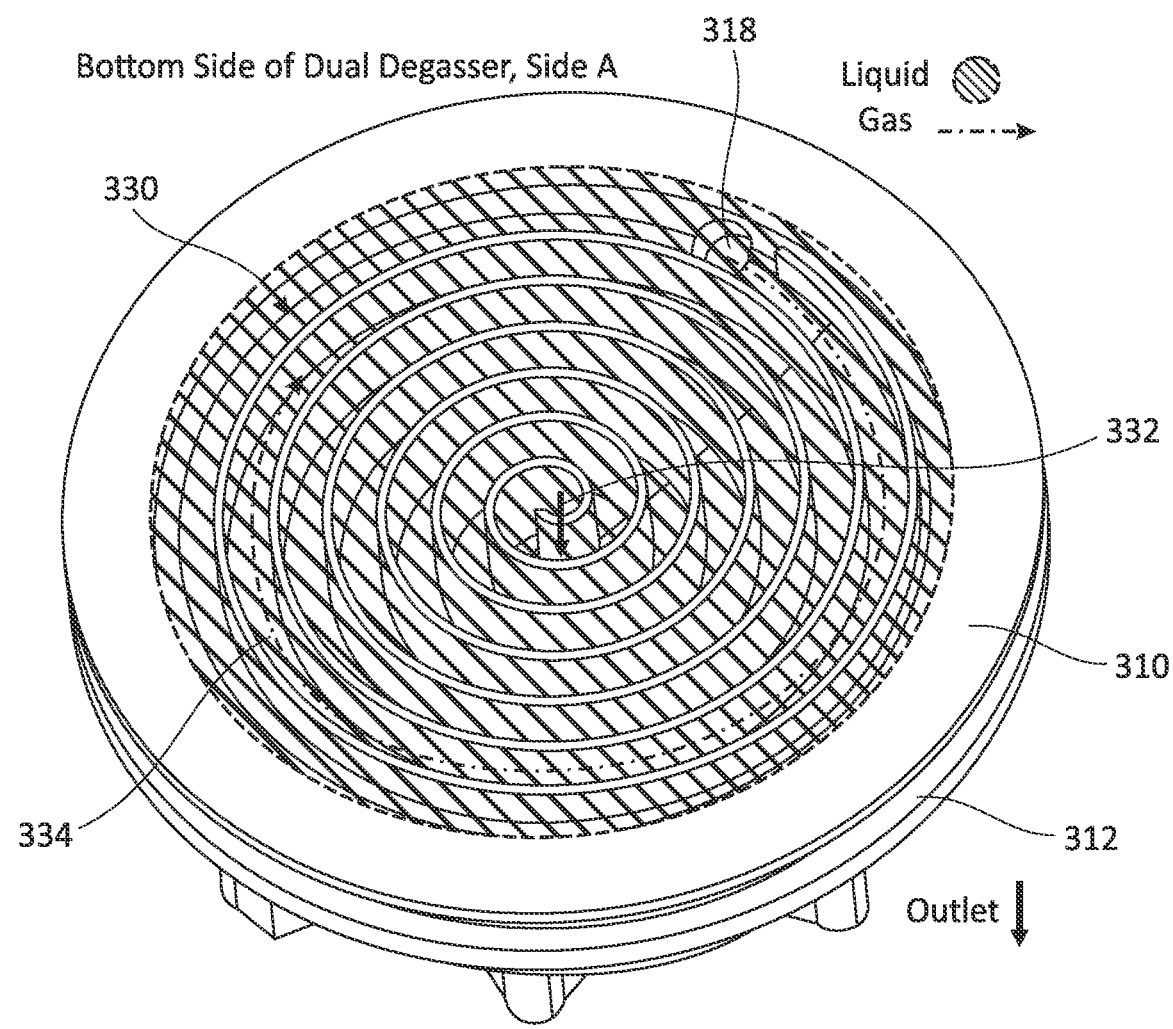
FIG. 2A is a bottom side perspective view of a portion of a degasser module.

As seen in FIG. 1A, pump 290 may pump a stream of ambient air through a microbial membrane filter 292 through an inlet 318. As seen in FIG. 2A, inside the container 316, the airstream 334 may be combined with the fluid pumped from the sorbent bed 294 into the lower fluid channel 330. The fluid may enter the lower fluid channel 330 anywhere along the pathway of the lower fluid channel 330. The addition of the airstream into the lower fluid channel 330 may cause the fluid and gas from the sorbent cartridge to follow the path defined by the lower fluid channel 330, leading to a port 332 that fluidly connects the lower fluid channel 330 and the upper fluid channel 340.

Figure 2B:
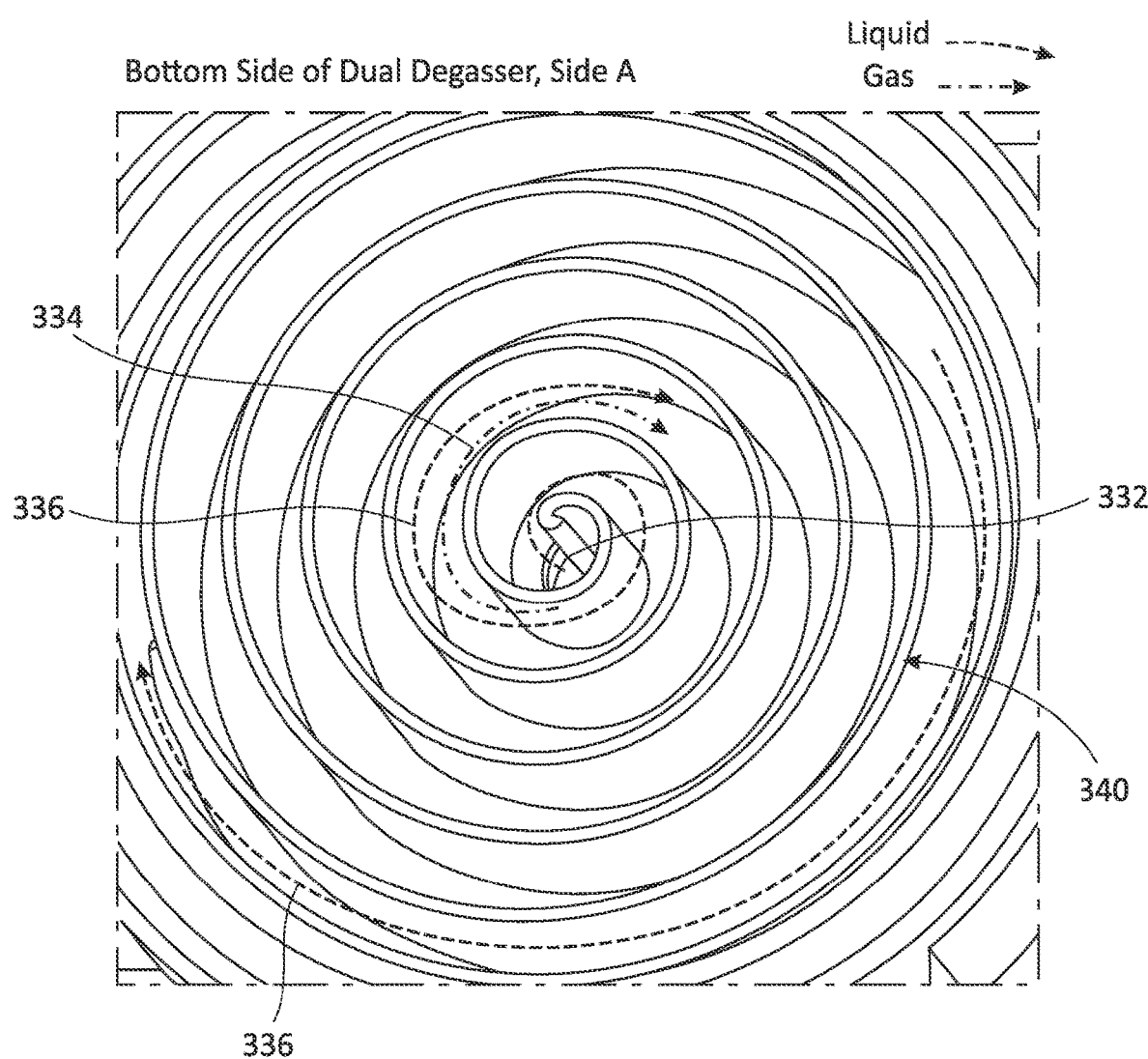
FIG. 2B is a top side perspective view of a portion of a degasser module.

Each of the lower fluid channel 330 and the upper fluid channels may be a long, narrow channel. Each fluid channel may be a length of at least about 6 inches, alternatively at least about 7 inches, alternatively at least about 8 inches, alternatively at least about 9 inches, alternatively at least about 10 inches, alternatively between about 6 inches and about 12 inches, alternatively between about 7 inches and about 11 inches, alternatively between about 8 inches and about 11 inches, alternatively between about 6 inches and about 25 inches, alternatively between about 6 inches and about 20 inches, alternatively between about 6 inches and about 15 inches in length. Each of the lower fluid channel 330 and the upper fluid channels may be in a spiral pattern (see, e.g., FIGS. 2A and 2B), a switchback pattern, random, or other suitable arrangement that first the length of the fluid path within the container 316. In embodiments where the patterns of the lower fluid channel 330 and the upper fluid channel 340 are spiral, the spiral of each may be either clockwise or counterclockwise from the center (e.g., as viewed from the top of the degassing unit 300). In some embodiments, the spirals of each may be in the same clockwise or counterclockwise direction or the spirals of each may be in different directions such that one is clockwise, and the other is counterclockwise.

Figure 3B:
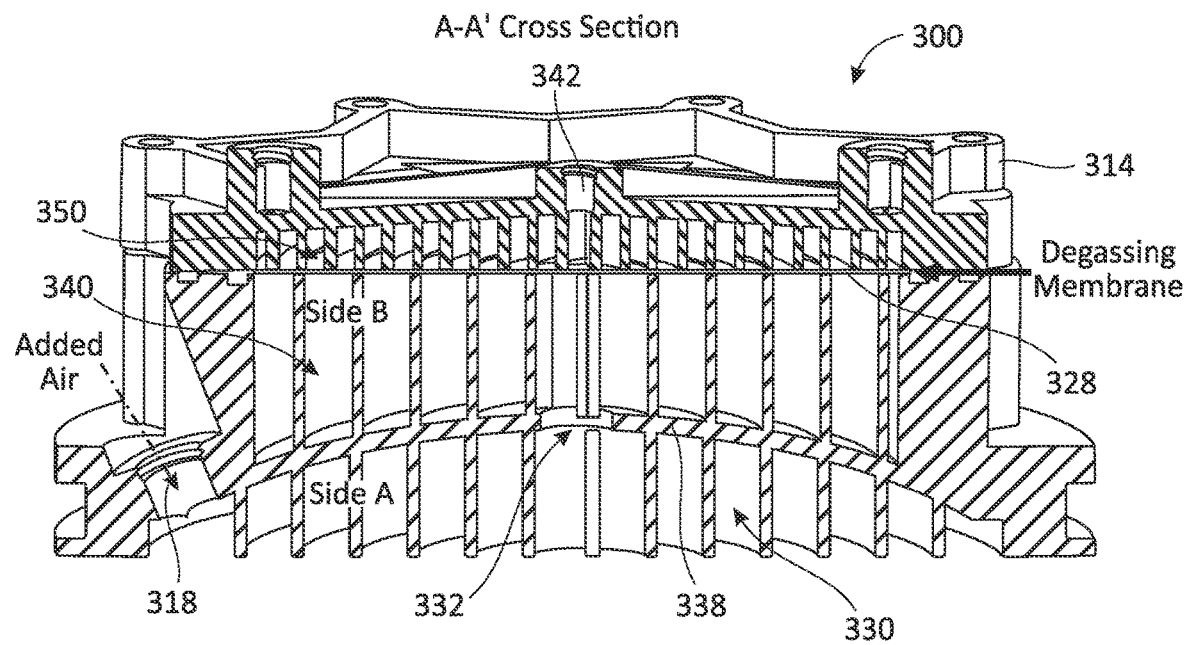
FIG. 3B is a cross-section A-A' of the degasser module shown in FIG. 3A.
Figure 3C:
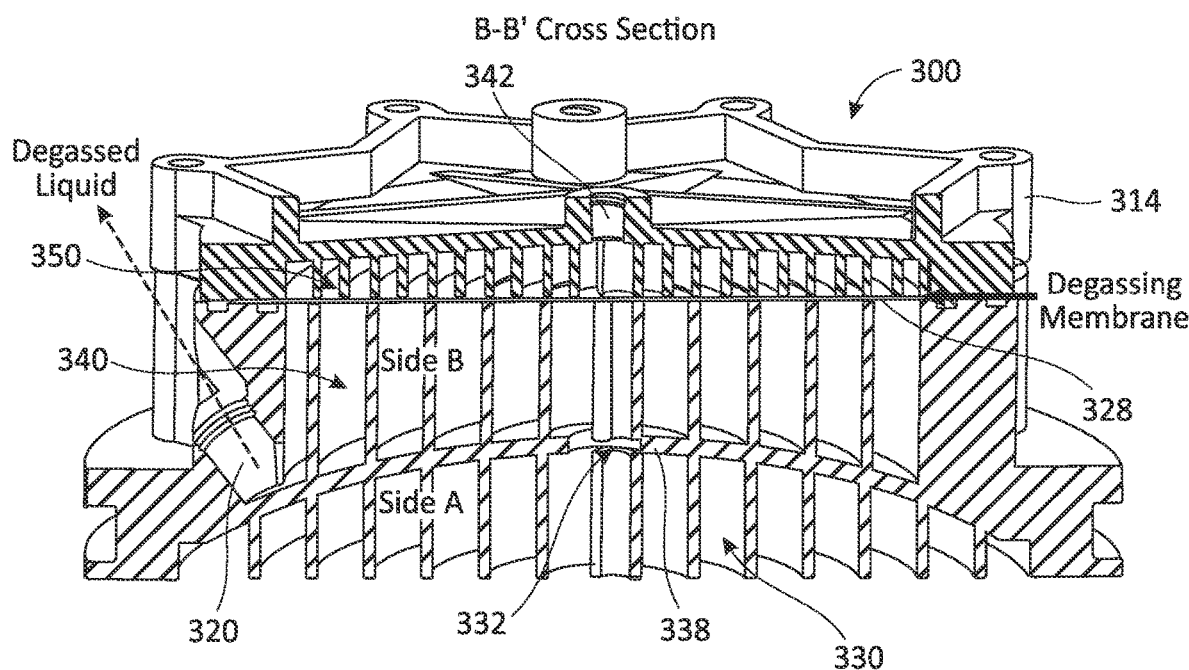
FIG. 3C is a cross-section B-B' of the degasser module shown in FIG. 3A.

As seen in FIGS. 1B, 3B, and 3C, a surface 338 separates the lower fluid channel 330 and the upper fluid channel 340 such that the lower 330 and upper 340 fluid channels are only in fluid communication through port 332. The surface 338 may have a dome (see, e.g., FIGS. 3B and 3C) or conical shape, such that the port 332 is at a greater height or elevation than an outer edge of the lower fluid channel 330. In some embodiments, the port may be at least about 0.125 inches, alternatively at least about 0.25 inches, alternatively at least about 0.4 inches, alternatively at least about 0.5 inches, alternatively between about 0.125 inches to about 0.8 inches, alternatively between about 0.125 inches to about 0.7 inches, alternatively between about 0.125 inches to about 0.6 inches, alternatively between about 0.125 inches to about 0.5 inches higher than an outer edge of the lower fluid channel 330. In embodiments where the surface has a dome shape, the port 332 may be located at or near the center of the dome. Thus, the surface 338 defining the top of the lower fluid channel 330 may have a concave surface and the surface 338 defining the bottom of the upper fluid channel 340 may have a convex surface. Alternatively, the surface 338 may be level, horizontal (not shown). In embodiments where the lower fluid channel 330 and the upper fluid channel 340 each have a spiral shape or pattern, the port 332 connecting the channels may be located at the center of each of the spirals and the air inlet port 318 and liquid outlet port 320 may be located at or near an outer edge of the lower fluid channel 330 and the upper fluid channel 340, respectively.

As seen in FIGS. 1A, 1B, and 2A, the air stream may be pumped through air inlet 318 into the lower fluid channel 330, where the air stream 334 may mix with the fluid, e.g., regenerated dialysate, in the lower fluid channel 330 that is being pumped up from the sorbent bed 294. The fluid may enter the lower fluid channel 330 anywhere along the pathway of the lower fluid channel 330. The flow rate of the ambient air stream into the degassing unit 300 may be between about 100 mL/min and about 600 mL/min, alternatively between about 200 mL/min and about 600 mL/min, alternatively between about 200 ml/min and about 500 mL/min, alternatively between about 200 mL/min and about 400 mL/min. The flow rate of the fluid and gas from the sorbent bed 294 may be between about 100 mL/min and about 600 mL/min, alternatively between about 200 mL/min and about 600 mL/min, alternatively between about 200 mL/min and about 500 mL/min, alternatively between about 200 mL/min and about 400 mL/min. In some embodiments, the flow rate of the ambient air and the flow rate of the fluid and gas from the sorbent bed 294 are substantially the same. Alternatively, the difference between the flow rate of the ambient air and the flow rate of the fluid may be between about 50 mL/min to about 100 mL/min, alternatively between about 50 mL/min to about 200 mL/min, alternatively between about 100 mL/min to about 300 mL/min, alternatively between about 100 mL/min to about 400 mL/min, alternatively between about 200 mL/min to about 400 mL/min, alternatively between about 300 mL/min to about 500 mL/min.

As seen in FIG. 2A, the path of the air stream 334 may force the fluid to flow along through the path defined by the lower fluid channel 330 until it reaches and flows through the port 332 to the upper fluid channel. The long path defined by the lower fluid channel 330 enables the mixing of the air stream 334 from the ambient air and the fluid, which contains $CO_2$. As the fluid flows through the lower fluid channel 330, the $CO_2$ partial pressure in the fluid (e.g., regenerated dialysate) may equilibrate with the ambient air, thereby lowering the total amount of dissolved $CO_2$. As explained above with reference to Henry's law, lowering the partial pressure of $CO_2$ for the liquid lowers the total amount of dissolved $CO_2$.

After exiting the lower fluid channel 330 through the port 332 into the upper fluid channel 340 through port 332, the fluid flows through the path 336 defined by the upper fluid channel 340 until it reaches liquid outlet port 320, which may be located at or near an outer edge of the upper fluid channel 340. A flow rate of the fluid at or near the center of the upper fluid channel 340 may be higher than a flow rate of the fluid at or near an outer edge of the upper fluid channel 340 due to a higher pressure near the center of the upper fluid channel 340. The long pathway defined by the upper fluid channel 340 allows at least a portion of the gas contained in the fluid to dissipate out of the fluid and into the atmosphere as the fluid follows path 336 through the upper fluid channel 340. The long length of the upper fluid channel 340 may give the gas and liquid time to separate. As the fluid containing the gas moves around the upper fluid channel (e.g., path 336 of the spiral channel shown in FIG. 2B), the fluid containing the gas may experience centripetal forces, which are greater on the liquid because of its greater mass as compared to a mass of the gas. This greater force required for changing the direction of the liquid may result in the liquid being forced against the outside of the upper fluid channel 340 (e.g., outer walls of the spiral depicted in FIG. 2B). This may help to collate small gas bubbles at the center of the upper fluid channel 340 or at the inner walls of the upper fluid channel 340, thereby allowing them to rise to a hydrophobic degassing membrane 328 because larger bubbles are less likely to remain mixed in the liquid stream or stick to surfaces. Thus, the centripetal force may help to separate the gas (e.g., $CO_2$) from the liquid. As the gas separates from the liquid in upper fluid channel 340, the gas may pass through the hydrophobic membrane 328 located above the upper fluid channel 340, while the liquid may exit out of the liquid outlet 320 at the bottom of the channel.

The hydrophobic degassing membrane 328 may be located on top of the upper fluid channel 340 and may be in contact with the fluid flowing through the upper fluid channel 340. Because it is hydrophobic, in general, fluid will not pass through the membrane 328 (i.e., it is impermeable to liquid), but will allow gas to pass through the membrane. The fluid contacting the hydrophobic membrane 328 may be under a modest amount of back pressure (e.g., <5 psi) allowing $CO_2$ and air bubbles to leave the fluid stream. The hydrophobic degassing membrane 328 may have a pore size between about 0.005 μm to about 1.5 μm, alternatively between about 0.005 μm to about 1.3 μm, alternatively between about 0.005 μm to about 1.0 μm, alternatively between about 0.006 μm to about 1.0 μm.

As seen in FIG. 3A, a cover 314 over the container 316 may be added to close the system and reduce environmental contaminants from entering the fluid. The cover 314 may contain an opening 342 to allow the gas (e.g., the $CO_2$ from the fluid) to escape into the atmosphere. As seen in FIGS. 1B, 3B, and 3C, the cover 314 may also contain an additional structure 350 to assist in keeping the hydrophobic membrane 328 substantially flat. Without the additional structure 350, the hydrophobic membrane 328 may form a curved, concave surface with a higher point in a center of the hydrophobic membrane 328 as compared to an outer edge of the hydrophobic membrane 328 due to pressure in the container 316. If the hydrophobic membrane 328 was no longer substantially flat, a portion of the hydrophobic membrane 328 may not be in contact with the liquid in the upper fluid channel 340. The additional structure 350 may be in any form that assists in keeping the hydrophobic membrane 328 substantially flat or planar, along with keeping some void space above the membrane to allow the gas to escape through the opening 342. The additional structure 350 may depend on the pattern of the upper fluid channel 340 as the additional structure 350 may complement the pattern of the upper fluid channel 340. For example, in embodiments where the upper fluid channel 340 is in a spiral configuration, the additional structure 350 may also be in a complementary spiral configuration, where at least a portion of the walls defining the spiral in the additional structure 350 may be positioned between the walls defining the spiral configuration of upper fluid channel 340, as seen in FIGS. 3B and 3C.

Various aspects of the present subject matter are set forth below, in review of, and/or in supplementation to, the embodiments described thus far, with the emphasis here being on the interrelation and interchangeability of the following embodiments. In other words, an emphasis is on the fact that each feature of the embodiments can be combined with each and every other feature unless explicitly stated otherwise or logically implausible. The embodiments described herein are restated and expanded upon in the following paragraphs without explicit reference to the figures.

In many embodiments, a degassing module is described. The degassing module may include an air inlet port, a fluid outlet port, first and second channels located in an interior chamber, wherein each of the first and second channels are configured to direct a flow of a fluid, wherein the first channel is in communication with the air inlet port and the second channel is in communication with the fluid outlet port, a port connecting the first and second channels, and a hydrophobic membrane positioned above the second channel.

In some embodiments, the degassing module further includes a cover with a gas outlet port, wherein the cover is positioned above the hydrophobic membrane.

In some embodiments, the first channel and the second channel each have a spiral configuration.

In some embodiments, the port connecting the first and the second channels is located at or near a center of first channel and at or near a center of the second channel.

In some embodiments, the first channel has a spiral configuration having a center of the spiral configuration and an outer edge, and wherein the air inlet port is located at the outer edge.

In some embodiments, the degassing module further includes a substrate separating the first and second channels, wherein the substrate comprises the port connecting the first and second channels. In some embodiments, the substrate comprises a dome shape, wherein the port is located approximately near the center of the dome shape.

In some embodiments, the second channel is located above the first channel.

In many embodiments, a system for dialysis is described. The system may include a sorbent regeneration cartridge comprising urease and a metal phosphate, a degassing module comprising: an air inlet port, a fluid outlet port, first and second channels located in an interior chamber, wherein each of the first and second channels are configured to direct a flow of a fluid, wherein the first channel is in communication with the air inlet port and the second channel is in communication with the fluid outlet port, a port connecting the first and second channels, and a hydrophobic membrane positioned above the second channel.

In some embodiments, the degassing module further includes a cover with a gas outlet port, wherein the cover is positioned above the hydrophobic membrane.

In some embodiments, the first channel and the second channel each have a spiral configuration.

In some embodiments, the port connecting the first and the second channels is located at or near a center of first channel and at or near a center of the second channel.

In some embodiments, the first channel has a spiral configuration having a center of the spiral configuration and an outer edge, and wherein the air inlet port is located at the outer edge.

In some embodiments, the degassing module further includes a substrate separating the first and second channels, wherein the substrate comprises the port connecting the first and second channels. In some embodiments, the substrate comprises a dome shape, wherein the port is located approximately near the center of the dome shape.

In some embodiments, the second channel is located above the first channel.

In some embodiments, the metal phosphate comprises zirconium phosphate.

In some embodiments, the metal phosphate comprises at least one of iron(III) phosphate, titanium(IV) phosphate, cerium(IV) phosphate, and combinations thereof.

In some embodiments, the metal phosphate comprises a mixture of at least two metal phosphates.

In some embodiments, metal phosphate comprises a mixture of zirconium phosphate and titanium phosphate.

In many embodiments, method of degassing a fluid comprising $CO_2$ is described. The method may include the step of pumping a flow of air into a stream of fluid into a first channel to form an aerated fluid stream, wherein the aerated fluid stream flows through a first channel, exits a port and flows through a second channel, and wherein bubbles of $CO_2$ are released from the aerated fluid in the second channel.

In some embodiments, the flow of air has a flow rate of between about 300 mL/min and about 500 mL/min.

In some embodiments, the method further includes the step of pumping the stream of fluid into the first channel, wherein the stream of fluid is pumped at a flow rate of between about 300 mL/min and about 500 mL/min.

In some embodiments, the flow rate of the stream of fluid is about the same as the flow rate of the flow of air into the first channel.

In some embodiments, the bubbles of $CO_2$ are released through a hydrophobic membrane. In some embodiments, the hydrophobic membrane is located on top of the second channel.

In some embodiments, the first channel has a spiral shape. In some embodiments, the second channel has a spiral shape. In some embodiments, the port is located at about a center of the spiral shape of the first channel and at about a center of the spiral shape of the second channel.

In some embodiments, the second channel is positioned on top of the first channel.

It should be noted that all features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the foregoing description does not explicitly state, in a particular instance, that such combinations or substitutions are possible. It is explicitly acknowledged that express recitation of every possible combination and substitution is overly burdensome, especially given that the permissibility of each and every such combination and substitution will be readily recognized by those of ordinary skill in the art.

As used herein and in the appended claims, the singular forms "a," "an," and "the" include plural referents unless the context clearly dictates otherwise.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the inventive scope of the claims by features, functions, steps, or elements that are not within that scope.

What is claimed:

1. A method of degassing a fluid comprising $CO_2$, comprising the steps of:
   pumping a flow of air into a stream of fluid in a first channel to form an aerated fluid stream,
   wherein the aerated fluid stream flows through the first channel, exits a port and flows through a second channel, and wherein $CO_2$ gas is released from the aerated fluid in the second channel.

2. The method of claim 1, wherein the flow of air has a flow rate of between about 300 mL/min and about 500 mL/min.

3. The method of claim 1, further comprising the step of pumping the stream of fluid into the first channel, wherein the stream of fluid is pumped at a flow rate of between about 300 mL/min and about 500 mL/min.

4. The method of claim 3, wherein the flow rate of the stream of fluid is about the same as a flow rate of the flow of air into the first channel.

5. The method of claim 1, wherein the $CO_2$ gas is released through a hydrophobic membrane located on top of the second channel.

6. The method of claim 5, wherein a cover comprising an outlet port is disposed above the hydrophobic membrane, and wherein the $CO_2$ gas is released through the outlet port.

7. The method of claim 5, wherein the hydrophobic membrane is in contact with the fluid stream in the second channel.

8. The method of claim 1, wherein the first channel has a spiral shape.

9. The method of claim 6, wherein the second channel has a spiral shape.

10. The method of claim 7, wherein the port is located at about a center of the spiral shape of the first channel and at about a center of the spiral shape of the second channel.

11. The method of claim 1, wherein the second channel is positioned on top of the first channel.

12. The method of claim 1, wherein the first channel and the second channel are separated by a substrate, and wherein the substrate comprises the port.

13. The method of claim 10, wherein the substrate comprises a dome shape, and wherein the port is located approximately near a center of the dome shape.

14. The method of claim 1, wherein the first channel has a spiral configuration having a center of the spiral configuration and an outer edge, and wherein the flow of air is pumped into an inlet port located at the outer edge.

15. The method of claim 1, wherein a fluid of the stream of fluid is a dialysate.

16. The method of claim 15, wherein the dialysate is degassed during a hemodialysis treatment.

* * * * *